(12) United States Patent
Anderson et al.

(10) Patent No.: US 6,555,337 B2
(45) Date of Patent: *Apr. 29, 2003

(54) NEUROGENIN

(75) Inventors: David J. Anderson, Altadena, CA (US); Qiufu Ma, Santa Monica, CA (US)

(73) Assignee: California Institute of Technology, Pasadena, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/722,570

(22) Filed: Sep. 27, 1996

(65) Prior Publication Data

US 2003/0044887 A1 Mar. 6, 2003

(51) Int. Cl.[7] .......................... C12N 5/10; C12N 15/12; C12N 15/63; C12P 21/02
(52) U.S. Cl. .................. 435/69.1; 435/320.1; 435/325; 536/23.5
(58) Field of Search ............................... 435/69.1, 325, 435/320.1; 536/23.5

(56) References Cited

PUBLICATIONS

Tapscott et al., *GenBank,* Accession No. V63842, Jul. 15, 1996.*

Ma et al., "Identification of neurogenin, a Vertebrate Neuronal Determination Gene," *Cell,* 87:43–52 (1996).

Sommer et al., "Neurogenins, A Novel Family of Atonal-–Related bHLH Transcription Factors, are Putative Mammalian Neuronal Determination Genes that Reveal Cell Heterogeneity in the Developing CNS and PNS," *Molecular and Cellular Neuroscience,* 8:221–241 (1996).

Akasawa et al., "A Mammalian Helix–Loop–Helix Factor Structurally Related to the Product of Drosophila Proneural Gene atonal Is a Positive Transcriptional Regulator Expressed in the Developing Nervous System," *J. Biol. Chem.,* 270:8730–8738 (1995).

Bartholoma et al., NEX–1: A Novel Brain–Specific Helix-Loop–Helix Protein with Autoregulation and Sustained Expression in Mature Cortical Neurons, *Mech. Devel.,* 48:217–228 (1994).

Jarman et al., "atonal Is A Proneural Gene That Directs Chordontonal Organ Formation in the Drosophila Peripheral Nervous System," *Cell,* 73:1307–1321 (1993).

Johnson et al., "Two Rat Homologues of Drosophila achaete–scute Specifically Expressed in Neuronal Precursors," *Nature,* 346:858–861 (1990).

Kume et al., "Molecular Cloning of a Novel Basic Helix-Loop–Helix Protein from the Rat Brain," *Biochem. Biophys. Res. Commun.,* 219:526–530 (1996).

Lee et al., "Conversion of Xenopus Ectoderm into Neurons by NeuroD, a Basic Helix–Loop–Helix Protein," *Science,* 268:836–844 (1995).

Naya et al., "Tissue–Specific Regulation of the Insulin Gene by a Novel Basic Helix–Loop–Helix Transcription Factor," *Genes & Dev.,* 9:1009–1019 (1995).

Shimizu et al., "MATH–2, a Mammalian Helix–Loop–Helix Factor Structurally Related to the Product of Drosophila Proneural gene atonal, is Specifically Expressed in the Nervous System," *Eur. J. Biochem.* 229:239–248 (1995).

Villares et al., "The achaete–scute Gene Complex of D. Melanogaster: Conserved Domains in a Subset of Genes Required for Neurogenesis and Their Homology to myc," *Cell,* 50:415–424 (1987).

* cited by examiner

*Primary Examiner*—Gary Kunz
*Assistant Examiner*—Stephen Gucker
(74) *Attorney, Agent, or Firm*—Mintz Levin Cohn Ferris Glovsky and Popeo, P.C.; Ivor R. Elrifi

(57) ABSTRACT

The invention relates to novel neurogenin proteins, nucleic acids and antibodies.

8 Claims, 6 Drawing Sheets

FIG. 1

```
  1 MPAPLETCTLSDLDCASSNSGSDLSSFLTDEEDCARLQPLASTSGLSVPAR  neurogenin
                  : :|||         :   :|||
  1 MVLLKCE..........YRDEEEDLTSASPCSVTSSFRSPAT           X-NGNR-1a 51 RSAPT.....LSGASNVPGGQDEEQER.RRRRGRARVRSEALLHSLRRSR   neurogenin
     :          :        ||:    |||  :  ::  : ::::|
 33 QTCSSDDEQLLSPTSPGQHQGEENSPRCRRSRGRAQGKSGETVLKIKKTR   X-NGNR-1a 95 RVKANDRERNRMHNLNAALDALRSVLPSFPDDTKLTKIETLRFAYNYIWA   neurogenin
    |||||:|||||||||||:|||:|| |||||:|||||||||||||||||||
 83 RVKANNRERNRMHNLNSALDSLREVLPSLPEDAKLTKIETLRFAYNYIWA   X-NGNR-1a 145 LAETLRLADQGLPGGGARERLLPPQCVPCLPGPPSPASDTESWGSGAAAS   neurogenin
    |:|||||| |   ::            ::                  ::
133 LSETLRLGDPVHRSASTPA........AAILVQDSSSSQSPSWSCSSSPS   X-NGNR-1a 195 PCATVASPLSDPSSPSASEDFTYGPGGPLFSFPGLPKDLLHTTPCFIPYH   neurogenin
     :  :       | : ||:||                  ::
175 SSCCSFSPASPASSTSDSIESWQPSELHLNPFMSASSAFI            X-NGNR-1a
```

FIG. 2

```
              <  basic   ><    helix-1    ><  loop  ><     helix-2       >
mNeurogenin   RSRRVKANDRERNRMHNLNAALDALRSVLP........SFPD.......DTKLTKIETLRFAYNYIWALAET
X-NGNR-1a     KTRRVKANNRERNRMHNLNSALDSLREVLP........SLPE.......DAKLTKIETLRFAYNYIWALSET
mNeuroD/BETA2 KLRRMKANARERNRMHGLNAALDNLRKVVP........CYSK.......TQKLSKIETLRLAKNYIWALSEI
mNex1/Math2   KFRRQEANARERNRMHGLNDALDNLRKVVP........CYSK.......TQKLSKIETLRLAKNYIWALSEI
rKW8          KLRRQKANARERNRMHDLNAALDNLRKVVP........CYSK.......TQKLSKIETLRLAKNYIWALSEI
mMath1        KNRRLAANARERRRMHGLNHAFDQLRNVIP........SFNN.......DKKLSKYETLQMAQIYINALSEI
D.Atonal      RKRRLAANARERRRMQNLNQAFDRLRQYLP........CLGN.......DRQLSKHETLQMAQTYISALGDL
rMash1        VARR...NERERNRVKLVNLGFATLREHVP........NG.........AANKKMSKVETLRSAVEYIRALQQL
D.AS-C T5     VIRR...NARERNRVKQVNNGFSQLRQHIPAAVIADLSNGRRGIGPGANKKLSKVSTLKMAVEYIRRLQKV
```

FIG. 3

(1). rat neurogenin cDNA sequence

```
   1 ATCCGGAGCT GATCTGATCG CCGGCGACAT CAGTCGGGAG ACCAGCCCGG
  51 CGCGTGGCCC CCTGCAGGCG AGGCGAGGAG GCCAAGCCCA TTCCCTCCCT
 101 GAGCCCCTGC GATCTTCCCC GGCCCTCGCG CCTGCAGCAG GCACAGGCTA
 151 GCCCCGGGTC ATACGGACAG TAAGTGCGCT TCGAAGGCCG TGCACTCGGC
 201 CCACATTCAA GCCCTCCAAA CCTCCCGTCC GTCCGTCCGT CCTGCAACGA
 251 TGCCTGCCCC TTTGGAGACC TGTCTCTCTG ACCTCGACTG CGCCAGCAGC
 301 AACAGCGGGA GCGACCTGTC CAGTTTCCTC ACCGACGAGG AGGACTGTGC
 351 CAGGCTCCAG CCCCTAGCTT CCACCTCAGG GCTGTCCGTG CCAGCCCGCA
 401 GGAGCGCGCC CACCCTCTCC GGGGCATCGA ACGTTCCCGG TGGCCAGGAC
 451 GAAGAGCAGG AGCGGCGGCG ACGGCGAGGT CGCGCGCGGG TGCGGTCCGA
 501 GGCGCTGCTG CACTCGCTGC GGAGGAGCCG TCGCGTCAAG GCCAACGATC
 551 GCGAGCGCAA CCGTATGCAT AACCTCAACG CTGCGCTGGA CGCTCTGCGC
 601 AGCGTGCTGC CCTCGTTCCC CGACGACACC AAGCTCACCA AGATTGAGAC
 651 GCTGCGCTTC GCCTACAACT ACATCTGGGC CCTGGCTGAG ACACTGCGCC
 701 TGGCAGATCA AGGGCTCCCG GGGGGCGGTG CCCGGGAGCG CCTCCTGCCT
 751 CCGCAGTGTG TCCCCTGCCT GCCCGGTCCC CGAGCCCGG CCAGCGATAC
 801 AGAGTCCTGG GGCTCCGGGG CCGCTGCCTC CCCCTGCGCT ACTGTGGCGT
 851 CACCACTCTC TGACCCCAGT AGTCCCTCGG CTTCAGAAGA CTTCACCTAT
 901 GGCCCGGGTG GTCCCCTTTT CTCCTTTCCT GGCCTGCCCA AAGACCTCCT
 951 CCATACGACA CCCTGCTTCA TCCCGTACCA CTAGGGCTTT GCAAGACAAC
1001 GTTAATACTT CTTTCCTGCC CCAGTCTATG AGCAATAGAT GGGGGAGCCG
1051 GCTGAAGCCT CGGGGAGCAC CCTTACCCCC AGGTGGATGC TGGGAGCTTT
1101 AAAGAGGGGA GGGATACCTG ACCACTTGCT AGGTTGCCGC ACCCTCGCTG
1151 AGAAGCTGCC CCTCGGACTG TTTCCCCACG CCCCAGCACC GGGCCCCTCC
1201 TGCCCGCCCC CCAGACGGGC TTTCGGTTTT TTTTTTGGAC TTCCTGAACT
1251 TCACAAAACC TCCTTTGTGA CTGGCTCAGA ACTGACCCCA GCCACCACTT
1301 CAGTGTGATT TGGAAAAGGG ACAGATGAGC CCCTGAAGAC GAGGTGAAAA
1351 GTCAATTTTA CAATTTGTAG AACTCTAATG AAGAAAAACG AGCATGAAAA
1401 TTCGGTTTGA GCCGGCTGAC AATACAATGA AAAGGCTTAA AAAAAAGGAG
1451 ACACAAGGAG TGGGCTTCAT GCATTATGGA TCCCGACCCC CACCACTGTG
1501 GGCTTGCTCC CGGAAGAACT GAGTGCT
```

FIG. 4

(2). Mouse neurogenin cDNA sequence (open reading frame)

```
  1 ATGCCTCCCC CTTTGGAGAC CTGCATCTCT GATCTCGACT
 51 GCTCCAGCAG CAACAGCAGC AGCGACCTGT CCAGCTTCCT CACCGACGAG
101 GAGGACTGTG CCAGGCTACA GCCCCTAGCC TCCACCTCGG GGCTGTCCGT
151 GCCAGCCCGG AGGAGCGCTC CCGCCCTCTC CGGGGCATCG AATGTTCCCG
201 GTGCCCAGGA CGAAGAGCAG GAACGGCGGA GGCGGCGAGG TCGCGCTCGG
251 GTGCGGTCCG AGGCTCTGCT GCACTCCCTG CGGAGGAGTC GTCGCGTCAA
301 AGCCAACGAT CGCGAGCGCA ACCGCATGCA CAACCTCAAC GCTGCGCTGG
351 ACGCCTTGCG CAGCGTGCTG CCCTCGTTCC CCGACGACAC CAAGCTCACC
401 AAGATTGAGA CGCTGCGCTT CGCCTACAAC TACATCTGGG CCCTGGCTGA
451 GACACTGCGC CTGGCAGATC AAGGGCTCCC CGGGGGCAGT GCCCGGGAGC
501 GCCTCCTGCC TCCGCAGTGT GTCCCTGTC TGCCCGGGCC CCCGAGCCCG
551 GCCAGCGACA CTGAGTCCTG GGGTTCCGGG GCCGCTGCCT CCCCCTGCGC
601 CACTGTGGCA TCACCACTCT CTGACCCCAG TAGTCCCTCG GCTTCAGAAG
651 ACTTCACCTA TGGCCCGGGC GATCCCCTTT TCTCCTTTCC TGGCCTGCCC
701 AAAGACCTGC TCCACACGAC GCCCTGTTTC ATCCCATACC ACTAGTAA
```

FIG. 5

(3). X-ngnr-1a cDNA sequence:

```
   1 GCGTGTCACA CGGCAGTTGC ACTCATAATA CACTGTGAGC TGACAGTCGC
  51 AACCACGCCC GACAGGGAAC ACGCAGCAAG TCTACTGCAC GACTATAACC
 101 CGACGACTCG ACCCAACTCA CCTGCTGCTT CAGGGGCCAA ACACCAAGTT
 151 ATAAAGTAAG TAACTTCCAT TGCAACTGCA GCATTGTCAC TTGCGACAGC
 201 GCATGAAGTA GTGAGAGGCA CAGACCATGT ACATATATGG GGTTTGTGGT
 251 TATTATAGTA AGTGGGATGA TGTTTGGGTT ATTATAGTAA GTGGATGTGA
 301 AGTTGTCAGT GCAACATTGG GGCTAACCAT TGGCTGTGTG TTTGCGCTTG
 351 TCTAGGATGG TGCTGCTCAA GTGCGAGTAC CGCGATGAAG AGGAGGACCT
 401 GACCTCTGCC TCCCCCTGCT CCGTGACCTC CTCTTTCCGT TCCCCGGCGA
 451 CGCAGACGTG CAGCTCGGAC GATGAGCAGC TCCTGAGTCC CACCAGCCCG
 501 GGACAGCACC AGGGGAAGA GAACAGCCCG CGATGCAGGA GGAGCCGAGG
 551 CCGCGCTCAG GGCAAGAGCG GAGAAACTGT GTTAAAGATC AAGAAGACCC
 601 GGCGCGTTAA AGCTAACAAC CGGGAAAGGA ATCGCATGCA CAACCTGAAC
 651 TCTGCGCTTG ATTCCCTCAG GGAAGTGTTG CCCTCTTTAC CTGAAGATGC
 701 CAAACTCACC AAGATAGAGA CCTTGCGCTT TGCCTACAAC TACATCTGGG
 751 CTCTTAGCGA AACTTTGCGC CTTGGCGACC CAGTGCACCG ATCTGCTTCC
 801 ACCCCAGCAG CAGCCATATT GGTGCAGGAC TCCTCTTCAT CCCAGAGCCC
 851 CTCCTGGAGC TGCAGCTCGT CCCCTTCTTC CTCTTGTTGC TCCTTCTCCC
 901 CGGCCAGCCC TGCCAGCTCC ACCTCGGACA GTATTGAGTC CTGGCAGCCC
 951 TCTGAGCTCC ACCTGAACCC CTTCATGTCT GCCAGCAGCG CTTTCATTTG
1001 AACTCCTGTT GGACTATGAT GGATTCTCAC ACTTCCAATT GCTACATATG
1051 AAGAATACCT CAGTGGGGCC CCAGTGCAAA TGATTTTCCT GGGAACCCAG
1101 TTTATTGAGC ATGAGCCCAT ATAGTGTAAT AATATCATCC TGCAGTGACC
1151 AAATTGCACT CTGTGGGTTC TGCTGATGGG GAGAAGTGGG GGGCTTGATC
1201 CCCTGAGTT TGTGCTTACC TGTATAGCAT TTACTCCCCC TGCTGTCATG
1251 CCCCTGGCAT ATGATGGAGT ACATTGCTGG GTCTATTTTA TTATCAGCAA
1301 TGTGAACTGA AA
```

FIG. 6

X-ngnr-1b cDNA sequence:

```
   1 CGAGTGCGCA ACACTTGAGC TGGAGTGCGG GGCGCGTGTC ACACACACAC
  51 TGAACTGCCA CTGACACCAG AGACACAGCG AGTGGGAACC CCCTGCTACT
 101 ACAGGACTAG GAGAAAAGCC GCACAGCCTG CAGCGCCGCA ACCCGACTCA
 151 CCTGCTGCTC CCGGAGCCAC AAGCCTGGCG CACAAGATGG TGCTGCTGAA
 201 GTGCGAATAC CGCGATGAGG TGTCGGAACT GACCTCTGTC TCCCCCTGCT
 251 CCGTGTCCTC CTCCTCTTCA CACCCGTCCC CGGCGATGCA GACGTGCAGC
 301 TCGGACGATG AGCAGCTACA CAGTCCGACA AGCCCGACGC TCACGCACCT
 351 GCAGCAGGGA CGGGACCAGG GGAGGAGAA CAGCCCGCGA TGCAGGAGGA
 401 GCCGAGCCCG CGGAGACACC GTGCTGAAGA TCAAGAAGAC CCGGCGCGTT
 451 AAAGCCAATA ACCGCGAGAG GAATCGCATG CACCACCTGA ACTATGCGCT
 501 CGATTCTCTG AGGGAGGTTC TACCGTCATT ACCCGAAGAC GCCAAACTCA
 551 CCAAGATAGA GACCTTGCGC TTTGCCCACA ACTACATCTG GGCTCTTAGC
 601 GAAACTTTGC GCCTGGCCGA CCAGCTGCAC GGATCTACTT CCACCCCAGC
 651 AGCAGCCATA TTGGTACAGG ACTCCTATCC TTCCCTGAGC CCCTCCTGGA
 701 GCTGCAGCTC GTCCCCATCC TCCAACTCTT GCGACTCCTT CTCCCCGACC
 751 AGCCCTGCCA GCTCCACCTC GGACAGTATT GAGTACTGGC AGCCCTCTGA
 801 GCTCCGCTTG AACCCCTTCA TGTCTGCCCT TTGAACGCAC AGGACTATGG
 851 GTGATTTTAA CTTTTTACAC TTTAAATTCC TGCTTCCCAT AAGGGTCAAG
 901 TACTGCAGGG GTTACATATC AAGTTTACCT CAGGGGGGGC CACAGCAAAT
 951 TCTTTTCCTG GGCCCTAAAA TGTCCTCTGA ATTTGAGCCC ATATAGTGCA
1001 ATGGTATAAC CCTGCAATGG TATAATCCAG CAATGGTATA ATCCTGCATC
1051 GTTACCTAAT TGTACTTTGT GGGGTCTGCT GATGGGGGAC AAGTGTTTGA
1101 CCTGTGTCCA GAGTTTCACA TTTACTCCCC CTTTTGGTAT ATCTCTGGCC
1151 GCAACACTTG CTGTGTCTGT TCATCGTTA GCTATGTGTA TTAGGAAACT
1201 GTCTATCCCT CATCTGCACC TGTTAGACTA CAGCTACCAA CTTCCTGTTA
1251 CCAGGGGGCT ACTGGGTAAT GTACTTC
```

NEUROGENIN

FIELD OF THE INVENTION

The invention relates to novel neurogenin proteins, nucleic acids and antibodies.

BACKGROUND OF THE INVENTION

Transcription factors in the basic-helix-loop-helix (bHLH) family have been shown to play a central role in cell type determination, in several tissues and organisms. For example, MyoD and myf5 are necessary and sufficient for mammalian myogenesis, while the proneural genes achaete-scute and atonal perform similar functions during Drosophila neurogenesis (for reviews, see (Weintraub, 1993; Jan and Jan, 1994)). In both vertebrate myogenesis and fly neurogenesis, multiple functionally-interchangeable bHLH proteins act in networks and/or cascades within their respective lineages (Jan and Jan, 1993). For example, at least four different bHLH proteins are sequentially expressed during murine muscle development: MyoD/myf5; myogenin and MRF4 (Olson and Klein, 1994). Similarly in Drosophila expression of achaete-scute is followed by that of asense during peripheral neurogenesis (Brand et al., 1993; Dominguez and Campuzano, 1993; Jarman et al., 1993a). The function of such cascades is not yet clear, although it has been suggested that the later-acting genes function in differentiation rather than in determination (Weintraub, 1993; Lee et al., 1995). Although numerous bHLH proteins expressed during vertebrate neurogenesis have been identified (Johnson et al., 1990; Akazawa et al., 1992; Ferreiro et al., 1992; Sasai et al., 1992; Ishibashi et al., 1993; Turner and Weintraub, 1994; Akazawa et al., 1995; Lee et al., 1995; Shimizu et al., 1995), none so far examined exhibits the functional properties expected of a neuronal determination factor ((Guillemot et al., 1993; Sommer et al., 1995); see below).

One feature that characterizes the proneural genes in Drosophila is their interaction with the genetic circuitry underlying lateral inhibition. Lateral inhibitory interactions between neuroectodermal cells, mediated by the products of the neurogenic genes Notch and Delta, result in the selection of a single sensory organ precursor (SOP) cell from a group of developmentally equivalent undetermined cells called a "proneural cluster" (Ghysen et al., 1993). All cells in the proneural cluster initially express achaete-scute, but during the selection process proneural gene expression becomes restricted at high levels to the SOP (Cubas et al., 1991). This restriction occurs because the proneural genes promote expression of Delta (Hinz et al., 1994; Kunisch et al., 1994), and their expression and function are in turn inhibited by signalling through Notch (for review, see (Ghysen et al., 1993)). Thus, cells which express sufficient achaete-scute, and hence Delta, to inhibit proneural activity in their neighbors adopt an SOP fate (for discussion, see (Chitnis, 1995)). In this way, the proneural genes both promote a neural fate cell-autonomously, and inhibit this fate non-autonomously.

Lateral inhibition mediated by vertebrate homologs of Notch and Delta has recently been demonstrated to regulate primary neurogenesis in Xenopus (Chitnis et al., 1995). Primary neurons differentiate in three parallel rows within the neural plate; between these rows undifferentiated neural plate cells are set aside for later waves of neurogenesis. Expression of X-Delta-1 defines three broader longitudinal domains that prefigure these territories of primary neurogenesis. Ectopic expression of a dominant negative form of X-Delta-1 (X-Delta-$1^{stu}$) increases the density of neurons that differentiate within each territory, but does not increase the width of each territory or the overall area of the neural plate (Chitnis et al., 1995). Conversely, expression of constitutively active forms of X-Notch-1 suppresses primary neurogenesis (Coffman et al., 1990; Coffman et al., 1993). These data suggest that the three territories of primary neurogenesis in Xenopus (medial, intermediate and lateral) are analogous to proneural clusters in Drosophila. This in turn implies the existence of one or more bHLH proteins whose expression defines these prospective neurogenic territories.

Several bHLH proteins expressed during Xenopus neurogenesis have been identified. One such protein, NeuroD, can exert a neuronal determination function when ectopically expressed, but the endogenous XNeuroD gene is not expressed early enough to play a proneural role (Lee et al., 1995). Several Xenopus homologs of achaete-scute have also been identified (Ferreiro et al., 1992; Zimmerman et al., 1993; Turner and Weintraub, 1994). Ectopic expression of one of these, XASH-3, can induce neural plate expansion (Ferreiro et al., 1994; Turner and Weintraub, 1994) or ectopic neurogenesis within the neural plate (Chitnis and Kintner, 1996), depending on the dose of injected RNA. Unlike NeuroD, however, XASH-3 is incapable of converting epidermal cells to neurons. Moreover, XASH-3 is expressed in a very restricted region of the neural plate, corresponding to the future sulcus limitans (Zimmerman et al., 1993). Thus, there must be other bHLH genes whose expression pattern and function are more consistent with proneural activity.

Accordingly, it is an object of the invention to provide such a bHLH gene, neurogenin. Thus, the invention provides recombinant neurogenin proteins and variants thereof, and to produce useful quantities of these neurogenin proteins using recombinant DNA techniques.

It is a further object of the invention to provide recombinant nucleic acids encoding neurogenin proteins, and expression vectors and host cells containing the nucleic acid encoding the neurogenin protein.

An additional object of the invention is to provide polyclonal and monoclonal antibodies directed against neurogenin proteins.

A further object of the invention is to provide methods for producing the neurogenin proteins.

SUMMARY OF THE INVENTION

In accordance with the objects outlined above, the present invention provides recombinant nucleic acids encoding neurogenin proteins.

In a further aspect, the invention provides expression vectors comprising transcriptional and translational regulatory DNA operably linked to DNA encoding a neurogenin protein, and host cells containing the expression vectors.

In an additional aspect, the invention provides methods for producing neurogenin proteins comprising the steps of culturing a host cell transformed with an expressing vector. comprising a nucleic acid encoding a neurogenin protein and expressing the nucleic acid to produce a neurogenin protein.

In a further aspect, the invention provides recombinant neurogenin proteins.

In a further aspect, the invention provides polyclonal or monoclonal antibodies to neurogenin proteins.

BRIEF DESCRIPTION OF THE DRAWINGS

FIG. 1 depicts the alignment of the amino acid sequences of rat neurogenin (top) (SEQ ID NO:1) and Xenopus (bottom; labelled X-NGNR-1.a) (SEQ ID NO:2) neurogenin. The bHLH region is marked in bold type. Solid lines indicated amino acid identity, the dots are conservative substitutions. Selection of the initiator methionine was according to Kozak's rule (Kozak, 1984), and identification of in-frame upstream termination codons (data not shown).

FIG. 2 depicts the alignment of the rat neurogenin bHLH domain (SEQ ID NO:3) with other bHLH domains (SEQ ID NOS:4–11). Identity is shown in bold type. References for the References for the compared sequences are: NeuroD (Lee et al., 1995)/BETA2 (Naya et al., 1995) (SEQ ID NO:5), MATH-2/Nex-1 (Bartholomä and Nave, 1994; Shimizu et al., 1995) (SEQ ID NO:6), MATH-1 (Akazawa et al., 1995) (SEQ ID NO:8), KW8 (Kume et al., 1996) (SEQ ID NO:7), Drosophila atonal (Jarman et al., 1993b) (SEQ ID NO:9), MASH1 (Johnson et al., 1990) (SEQ ID NO:10), AS-C T5 (Villares and Cabrera, 1987) (SEQ ID NO:11).

FIG. 3 depicts the nucleic acid sequence of rat neurogenin (SEQ ID NO:12); the protein sequence is easily determined.

FIG. 4 depicts the nucleic acid sequence of mouse neurogenin (SEQ ID NO:13) the protein sequence is easily determined.

FIG. 5 depicts the nucleic acid sequence of one of the Xenopus neurogenin isoforms (SEQ ID NO:14); the protein sequence is easily determined.

FIG. 6 depicts the nucleic acid sequence of the other Xenopus neurogenin isoforms (SEQ ID NO:15); the protein sequenceis easily determined.

DETAILED DESCRIPTION OF THE INVENTION

The present invention provides novel neurogenin proteins. In a preferred embodiment, the neurogenin proteins are from vertebrates, more preferably from mammals, and in the preferred embodiment, from rats, mice or humans. However, using the techniques outlined below, neurogenin proteins from other organisms may also be obtained.

A neurogenin protein of the present invention may be identified in several ways. A neurogenin nucleic acid or neurogenin protein is initially identified by substantial nucleic acid and/or amino acid sequence homology to the sequences shown in the Figures. Such homology can be based upon the overall nucleic acid or amino acid sequence.

As used herein, a protein is a "neurogenin protein" if the overall homology of the protein sequence to the amino acid sequences of the neurogenins depicted herein is preferably greater than about 40%, more preferably greater than about 60% and most preferably greater than 80%. In some embodiments the homology will be as high as about 95 or 98%. This homology will be determined using standard techniques known in the art, such as the Best Fit sequence program described by Devereux et al., Nucl. Acid Res. 12:387–395 (1984) or the BLASTX program (Altschul et al., J. Mol. Biol. 215, 403–410). The alignment may include the introduction of gaps in the sequences to be aligned. In addition, for sequences which contain either more or fewer amino acids than the proteins disclosed herein, it is understood that the percentage of homology will be determined based on the number of homologous amino acids in relation to the total number of amino acids. Thus, for example, homology of sequences shorter than that shown in the Figures, as discussed below, will be determined using the number of amino acids in the shorter sequence.

Neurogenin proteins may be identified in one aspect by significant homology to the areas other than the bHLH domain, i.e. the N- and C-terminal portions of the sequences depicted in the Figures. This homology is preferably greater than about 40%, with greater than about 50 or 60% being particularly preferred and greater than about 80% being especially preferred. In some cases the homology will be greater than about 90 to 95 or 98%.

In addition, a neurogenin protein preferably also has significant homology to the neurogenin bHLH domain as described herein. This homology is preferably greater than about 75%, with greater than about 80% being particularly preferred and greater than about 85% being especially preferred. In some cases the homology will be greater than about 90 to 95 or 98%.

Neurogenin proteins of the present invention may be shorter or longer than the amino acid sequences shown in the Figures. Thus, in a preferred embodiment, included within the definition of neurogenin proteins are portions or fragments of the sequences depicted herein.

Neurogenin proteins may also be identified as being encoded by neurogenin nucleic acids. Thus, neurogenin proteins are encoded by nucleic acids that will hybridize to the sequences depicted in FIGS. 3 (SEQ ID NO:12), 4 (SEQ ID NO:13), 5 (SEQ ID NO:14), or 6 (SEQ ID NO:15), as outlined herein.

In a preferred embodiment, when the neurogenin protein is to be used to generate antibodies, the neurogenin protein must share at least one epitope or determinant with one or more of the full length proteins depicted herein. By "epitope" or "determinant" herein is meant a portion of a protein which will generate and/or bind an antibody. Thus, in most instances, antibodies made to a smaller neurogenin protein will be able to bind to the full length protein. In a preferred embodiment, the epitope is unique; that is, antibodies generated to a unique epitope show little or no cross-reactivity, for example, with other bHLH domains. The neurogenin antibodies of the invention specifically bind to neurogenin proteins. By "specifically bind" herein is meant that the antibodies bind to the protein with a binding constant in the range of at least $10^4$–$10^6$ $M^{-1}$, with a preferred range being $10^7$–$10^9$ $M^{-1}$.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequences of FIGS. 3, 4, 5, and 6 is preferably greater than about 40%, more preferably greater than about 50%, particularly greater than about 60% and most preferably greater than 75%. In some embodiments the homology will be as high as about 80 to 90 to 95 or 98%.

In a preferred embodiment, a neurogenin nucleic acid encodes a neurogenin protein. As will be appreciated by those in the art, due to the degeneracy of the genetic code, an extremely large number of nucleic acids may be made, all of which encode the neurogenin proteins of the present invention. Thus, having identified a particular amino acid sequence, those skilled in the art could make any number of different nucleic acids, by simply modifying the sequence of one or more codons in a way which does not change the amino acid sequence of the neurogenin.

In one embodiment, the nucleic acid homology is determined through hybridization studies. Thus, for example, nucleic acids which hybridize under high stringency to the nucleic acid sequences shown in the Figures or their complements are considered neurogenin genes. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference.

In another embodiment, less stringent hybridization conditions are used; for example, moderate or low stringency conditions may be used, as are known in the art; see Maniatis and Ausubel, supra.

The neurogenin proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated neurogenin nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a neurogenin protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Also included with the definition of neurogenin protein are other neurogenin proteins of the neurogenin family, and neurogenin proteins from other organisms, which are cloned and expressed as outlined below. Thus, probe or degenerate polymerase chain reaction (PCR) primer sequences may be used to find other related neurogenin proteins from humans or other organisms. As will be appreciated by those in the art, particularly useful probe and/or PCR primer sequences include the unique areas of the neurogenin nucleic acid sequence. Thus, useful probe or primer sequences may be designed to the bHLH domain or the N- and C-terminal portions of the sequence. As is generally known in the art, preferred PCR primers are from about 15 to about 35 nucleotides in length, with from about 20 to about 30 being preferred, and may contain inosine as needed. The conditions for the PCR reaction are well known in the art.

Once the neurogenin nucleic acid is identified, it can be cloned and, if necessary, its constituent parts recombined to form the entire neurogenin protein nucleic acid. Once isolated from its natural source, e.g., contained within a plasmid or other vector or excised therefrom as a linear nucleic acid segment, the recombinant neurogenin nucleic acid can be further used as a probe to identify and isolate other neurogenin nucleic acids. It can also be used as a "precursor" nucleic acid to make modified or variant neurogenin nucleic acids and proteins.

Using the nucleic acids of the present invention which encode a neurogenin protein, a variety of expression vectors are made. The expression vectors may be either self-replicating extrachromosomal vectors or vectors which integrate into a host genome. Generally, these expression vectors include transcriptional s and translational regulatory nucleic acid operably linked to the nucleic acid encoding the neurogenin protein. "Operably linked" in this context means that the transcriptional and translational regulatory DNA is positioned relative to the coding sequence of the neurogenin protein in such a manner that transcription is initiated. Generally, this will mean that the promoter and transcriptional initiation or start sequences are positioned 5' to the neurogenin protein coding region. The transcriptional and translational regulatory nucleic acid will generally be appropriate to the host cell used to express the neurogenin protein; for example, transcriptional and translational regulatory nucleic acid sequences from Bacillus are preferably used to express the neurogenin protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The neurogenin proteins of the present invention are produced by culturing a host cell transformed with an expression vector containing nucleic acid encoding a neurogenin protein, under the appropriate conditions to induce or cause expression of the neurogenin protein. The conditions appropriate for neurogenin protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells.

In a preferred embodiment, the neurogenin proteins are expressed in mammalian cells. Mammalian expression systems are also known in the art. A mammalian promoter is any DNA sequence capable of binding mammalian RNA polymerase and initiating the downstream (3') transcription of a coding sequence for neurogenin protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include the use of viruses such as retroviruses and adenoviruses, dextran-mediated transfection, calcium phosphate precipitation, polybrene mediated transfection, protoplast fusion, electroporation, encapsulation of the polynucleotide(s) in liposomes, and direct microinjection of the DNA into nuclei.

In a preferred embodiment, neurogenin proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of neurogenin protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the neurogenin protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, neurogenin proteins are produced in insect cells. Expression vectors for the transformation of insect cells, and in particular, baculovirus-based expression vectors, are well known in the art.

In a preferred embodiment, neurogenin protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The neurogenin protein may also be made as a fusion protein, using techniques well known in the art. Thus, for example, for the creation of monoclonal antibodies, if the desired epitope is small, the neurogenin protein may be fused to a carrier protein to form an immunogen. Alternatively, the neurogenin protein may be made as a fusion protein to increase expression, or for other reasons.

Also included within the definition of neurogenin proteins of the present invention are amino acid sequence variants. These variants fall into one or more of three classes: substitutional, insertional or deletional variants. These variants ordinarily are prepared by site specific mutagenesis of nucleotides in the DNA encoding the neurogenin protein, using cassette or PCR mutagenesis or other techniques well known in the art, to produce DNA encoding the variant, and thereafter expressing the DNA in recombinant cell culture as outlined above. However, variant neurogenin protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the neurogenin protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed neurogenin variants screened for the optimal combination of desired activity. Techniques for making substitution mutations at predetermined sites in DNA having a known sequence are well known, for example, M13 primer mutagenesis and PCR mutagenesis. Screening of the mutants is done using assays of neurogenin protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the neurogenin protein are desired, substitutions are generally made in accordance with the following chart:

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the neurogenin proteins as needed. Alternatively, the variant may be designed such that the biological activity of the neurogenin protein is altered.

In one embodiment, bHLH variants are made. In one embodiment, the bHLH domain may be eliminated entirely. Alternatively, any or all of the amino acids of a bHLH domain may be be altered or deleted. In a preferred embodiment, one or more of the amino acids of the domain are substituted by other amino acids. Thus, amino acids corresponding to the neurogenin bHLH domain residues may be altered.

In one embodiment, the neurogenin nucleic acids, proteins and antibodies of the invention are labelled. By "labelled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the neurogenin protein is purified or isolated after expression. Neurogenin proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the neurogenin protein may be purified using a standard anti-neurogenin antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the neurogenin protein. In some instances no purification will be necessary.

Once expressed and purified if necessary, the neurogenin proteins are useful in a number of applications as will be apparent to those in the art. For example, the proteins may be used to generate antibodies, which are then useful to purify the protein as outlined above. The antibodies are useful in diagnositic assays to detect neurogenin proteins. The proteins are also useful in neurogenesis.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Cloning of Rat and Xenopus Genes

Previous work has identified MASH1 as a bHLH protein expressed in autonomic but not sensory ganglia of the mammalian PNS (Johnson et al., 1990; Lo et al., 1991; Guillemot and Joyner, 1993; Guillemot et al., 1993). We sought to isolate cDNAs encoding bHLH proteins expressed, conversely, in sensory but not autonomic ganglia. Degenerate RT-PCR was performed using cDNA prepared from embryonic day 13.5 (E13.5) rat dorsal root ganglia (DRG), using oligonucleotide primers derived from conserved regions of bHLH subfamilies including MASH1 and NeuroD. Random-primed cDNA template prepared from E13.5 rat embryonic DRGs was subjected to 40 cycle of PCR (1' @ 94° C.; 2' @ 45° C.; 2' @ 65° C.). The 5' primers were:

5'CGCGGATCC(A/C)GNAA(C/T)GA(A/G)(A/C)G(G/C/T)GA(A/G)(A/C)3' (SEQ ID NO:16) and

5'CGCGGATCCGCNAA(C/T)GC(A/C/T)(A/C)G(G/CT)GA(A/G)(A/C)G (SEQ ID NO:17), which were derived from RNERER and ANARER, respectively, and contain a BamH1 site at the end. The 3' primers were 5'CCGGAATTCGT(T/C)TC(A/G/C)A(T/C)(T/C)TT(A/G)CT(A/C/G)A(A/G/T)(T/C)TT3', (SEQ ID NO:18) and 5'CCGGAATTCGT(T/C)TC(A/G/C)A(T/C)(T/C)TT(A/G/T)GA(A/C/G)A(A/G/T)(T/C)TT3' (SEQ ID NO:19), both of which are the reverse translation of K(L/M)SK(V/I)ET (SEQ ID NO:20) and contain a EcoRI site at the end. The 130 bp-PCR product was purified from a polyacrylamide gel, cloned into M13mp19 (New England Bio-labs), and sequenced. The ngn PCR product was then used to screen a lambda ZAP cDNA library prepared from rat E13.5 DRG (Saito et al., 1995). The isolated 1.2 kb and 1.7 kb cDNA clones were sequenced on both strands by Caltech sequencing core facility. The 1.7 kb cDNA fragment, encoding a predicted protein of 244 amino acid residues, was then used to screen a mouse lambda-2 129 genomic library (a gift of Z. Chen). From a 17-kb positive clone, a 2.0 kb fragment hybridizing to rat ngn cDNA was isolated and sequenced, which contains an open reading frame (ORF) differing from the rat one at six positions. The 2.2 kb-X-ngnr-1.a cDNA was isolated by screening a Xenopus St 17 cDNA library (Kintner and Melton, 1987) at low stringency using the rat cDNA as probe. An isoform of X-ngnr-1.a called X-ngnr1.b was also isolated from this screen, and is depicted in the figures. X-ngnr-1.a and X-ngnr-1.b show the same expression patterns and phenotypes in mRNA injection (data not shown), and are referred to collectively as X-NGNR-1 in the text. Nucleotide sequences of the rat, mouse and two isoforms of the Xenopus neurogenin (SEQ ID NO:16)have been deposited in GeneBank database, with accession numbers U67777, U67776, U67778 and U67779, respectively.

Preliminary experiments indicated that mouse ngn mRNA caused ectopic neurogenesis when microinjected into Xenopus embryos (not shown), a phenotype similar to that obtained by over-expression of NeuroD (Lee et al., 1995). To determine whether this phenotype reflected the esixtence of a Xenopus gene with similar functional characteristics, the murine ngn cDNA probe was used to screen a stage 17 (St.17) Xenopus cDNA library at low-stringency. Several ngn-related cDNAs were obtained. This cDNA, which we have named Xenopus ngn-related-1 (X-ngnr-1), encodes a polypeptide of 215 amino acids displaying 82% sequence identity to mouse neurogenin within the bHLH domain (FIG. 2).

Example 2

Expression of Neurogenin During Neurogenesis

Non-radioactive in situ hybridization to frozen sections of mouse embryos was performed as previously described (Birren et al., 1993). Whole-mount in situ hybridization was performed essentially as described (Chitnis et al., 1995) using digoxigenin-labelled antisense probes for X-NGNR-1, XNeuroD (Lee et al., 1995), X-Delta-1 and N-tubulin (Chitnis et al., 1995), with the following modification. At the step of developing the alkaline phosphatase reaction using NBT/BCIP substrates, 0.45 $\mu$l rather than 4.5 $\mu$l of NBT stock solution (75 mg/ml in 70% dimethyl formamide) was added to each 1 ml of staining buffer. This change reduced background staining and improved visualization of low-abundance mRNAs.

A preliminary analysis of ngn mRNA expression in mouse embryos by in situ hybridization revealed that expression of this gene is apparently restricted to the nervous-system (data not shown). Within the nervous system, the expression of neurogenin is spatially or lineally restricted; for example it is expressed in the ventral half of the spinal cord, except for a narrow domain just below the roofplate. In the peripheral nervous system, ngn mRNA is expressed in developing sensory but not in autonomic ganglia. Interestingly, a comparison of the expression of ngn and NeuroD expression on adjacent serial sections revealed that the two genes appear to be sequentially expressed in overlapping regions or neural cell populations. In the ventral spinal cord, for example, ngn mRNA is expressed throughout the ventricular zone, in regions where uncommitted progenitors are located, while NeuroD transcripts are expressed at the lateral border of the ventricular zone. However both genes show a similar dorsoventral restriction in their domains of expression within the spinal cord (except that NeuroD is not expressed below the roof plate). A similar spatial segregation is seen in the mesencephalic-diencephalic region. These data suggest that neurogenin and NeuroD may function in similar regions of the murine nervous system but at sequential stages of neurogenesis.

A similar spatial overlap but temporal displacement was found for the expression of X-ngnr-1 and ANeuroD in Xenopus. For example, at St. 12, X-ngnr-1 expression is observed in three broad patches within the neural plate, that demarcate the medial, intermediate and lateral territories where primary motorneurons, intemeurons and sensory neurons, respectively, will later differentiate. In contrast, no XNeuroD expression is yet detected at this stage, nor have any primary neurons yet differentiated. XNeuroD mRNA can be detected at St. 13.5, in narrow rows of cells located within the three domains of primary neurogenesis which is already underway at this time. At this stage, X-ngnr-1 is expressed in a similar region of the neural plate but in many more cells than XNeuroD. A similar sequential expression of X-NGNR-1 and XNeuroD is seen in the trigeminal placode. Thus in Xenopus and in mouse, expression of neurogenin/X-NGNR-1 preceeds but spatially overlaps that of NeuroD/XNeuroD.

Example 3

Inducement of Neurogenesis

The observation that expression of X-ngnr-1 temporally and spatially prefigures the expression of XNeuroD, taken together with the sequence homology between the two genes, led us to test whether expression of X-NGNR-1 like that of XNeuroD is sufficient to induce premature and/or ectopic primary neurogenesis. We therefore injected X-ngnr-1 mRNA into one blastomere of two-cell stage embryos, and examined the pattern of neurogenesis after further development by whole mount in situ hybridization using a probe for N-tubulin, a neuron-specific marker in Xenopus (Chitnis et al., 1995). The distribution of β-galactosidase activity translated from a co-injected lacZ mRNA, as determined by counterstaining with XGal, was used to assess the overall distribution of the injected mRNAs in each individual embryo. Two types of negative controls were used: the uninjected side of the same embryo, and separate embryos injected only with lacZ mRNA.

The X-NGNR-1 open reading frame was cloned in-frame into the EcoR1 site of the vector pMT-CS2 (Turner and Weintraub, 1994). Capped X-NGNR-1 mRNA was transcribed using SP6 RNA polymerase as decribed (Kintner and Melton, 1987). X-NGNR-1 mRNA was co-injected with lacZ mRNA (as a marker) into one blastomeres of two-celled embryos (Coffman et al., 1993). Notch$^{ICD}$ and X-Delta-1$^{stu}$ RNAs were prepared as described (Chitnis et al., 1995). Injection of LacZ mRNA alone was done as a control. Histochemical staining for β-galactosidase was performed to visualize the distribution of injected mRNAs. Embryos were collected at the neural plate stage (St13–14) or tail-bud stage (St 26) and subjected to in situ hybridization using probes as indicated in the figure legends. Animal cap assays were performed as described previously (Ferreiro et al., 1994).

Over-expression of X-ngnr-1 mRNA caused extensive ectopic neurogenesis within the neural plate (100% of embryos examined; ≧100 embryos injected). At St. 13.5, for example, nearly every cell on the injected side of the embryo appeared to express N-tubulin, whereas on the uninjected side the three stripes of primary neurogenesis were clearly distinguishable (data not shown); moreover within these stripes the distribution of neurons was more scattered than on the injected side. In addition to the increased extent of neurogenesis, the timing of neuronal differentiation was accelerated on the injected side, so that N-tubulin$^+$ cells were seen on the injected side at St. 12.5, a time at which no expression of this marker was detected on the contralateral control side (not shown). Moreover, X-ngnr-1 also caused ectopic neuronal differentiation in regions of non-neurogenic ectoderm that flank the neural plate. The consequence of this was most easily observed at St. 24–26 (tail bud stage), where supernumerary neurons were observed within the epidermis. Extensive ectopic neurogenesis was also observed in the most anterior part of the embryo, where for example the eye was missing and replaced by amorphous neural tissue (data not shown). In these respects, the phenotype of X-ngnr-1 mRNA-injected embryos appeared similar or identical to that previously reported for XNeuroD (Lee et al., 1995). In the latter case, it has been confirmed by injections at the 32-cell stage that the ectopic neurons in the skin indeed reflect a conversion of non-neurogenic ectoderm (and not, for example, simply conversion of migrating trunk neural crest cells) (Lee et al., 1995), and we infer by extension that the same holds true for X-NGNR-1-injected embryos.

The fact that over-expression of X-ngnr-1 yielded an XNeuroD-like phenotype, coupled with the fact that endogenous X-ngnr-1 expression temporally preceeds and overlaps that of XNeuroD, suggested that the latter might be a target of transcriptional activation by the former. To test this, embryos injected with X-ngnr-1 mRNA were hybridized with an XNeuroD probe. A massive, ectopic induction of endogenous XNeuroD mRNA was observed in X-ngnr-1 mRNA-injected embryos (100% of embryos examined; >50 embryos injected). The extent of ectopic expression was similar to that observed with an N-tubulin probe. By contrast, injection of XNeuroD mRNA did not increase the expression of endogenous X-ngnr-1 mRNA, although it did induce ectopic neurogenesis as previously reported (Lee et al., 1995). These data suggest that the neurogenic phenotype of X-ngnr-1 mRNA-injected embryos may reflect an induction of endogenous XNeuroD, and suggest that the sequential expression of these two genes during Xenopus neurogenesis reflects a unidirectional cascade in which the former induces transcription of the latter.

To ensure that the ectopic neurogenesis promoted by injection of X-NGNR-1 RNA was not a secondary consequence of induction of mesodermal tissue, we performed animal cap experiments. Animal caps from embryos injected in both blastomeres with various RNAs at the 2-cell stage were dissected and allowed to develop in vitro, after which time they were assayed for expression of various marker mRNAs by RNase protection (Ferreiro et al., 1994). As expected from the whole mount in situ analysis, injection of X-NGNR-1 RNA caused induction of expression of N-tubulin mRNA. No mesodermal induction was detected under these conditions, by criteria of expression of muscle-specific actin mRNA (Ferreiro et al., 1994). This control experiment indicates that the promotion of neurogenesis by X-NGNR-1 is a direct effect on naive ectoderm, and not an indirect result of mesoderm induction.

The effect of X-NGNR-1 was also compared to that of noggin (Smith and Harland, 1992) in the animal cap experiments. Noggin, which promotes neural induction (Lamb et al., 1993) by antagonizing the epidermalizing effect of BMP-4 (Sasai et al., 1995), induced expression of NCAM, a marker of undifferentiated neural tissue (Kintner and Melton, 1987), but not of the neuronal differentiation marker N-tubulin (Chitnis et al., 1995). X-NGNR-1, by contrast, induced expression of both NCAM and N-tubulin mRNAs, although the level of the latter transcript was higher. These data are consistent with the idea that noggin promotes neuralization but is insufficient for neuronal differentiation (Ferreiro et al., 1994), while X-NGNR-1 promotes both neuralization and consequent neuronal differentiation.

X-NGNR-1 Expression Preceeds, and Can Activate Expression of, X-Delta-1 The foregoing data indicated that X-ngnr-1 is expressed earlier than XNeuroD, and is capable of inducing expression of XNeuroD as well as of promoting ectopic neurogenesis. Thus, like NeuroD, X-NGNR-1 can exert a neuronal determination function when over-expressed. But can X-NGNR-1 normally play this role in vivo? To address this question we examined the timing of X-NGNR-1 expression relative to that of X-Delta-1. In Xenopus as in Drosophila, X-Delta-1 encodes a lateral inhibitory ligand that controls a choice between neuronal and non-neuronal fates (Chitnis et al., 1995). By definition, therefore, at the time Delta is first expressed this choice has not yet been made.

During early gastrulation (St. 10.5), X-ngnr-1 mRNA can be detected at the lateral margins of the prosepctive neural plate. At this stage, X-Delta-1 mRNA is not yet expressed in this region, although it is detected in an area adjacent to the blastopore. By midgastrulation (St. 11.5), both X-ngnr-1 and X-Delta-1 mRNAs can be detected in three distinct patches within the neural plate, prefiguring the regions where primary neurogenesis will occur. Within these regions the domain of X-ngnr-1 expression appears to encompass that of X-Delta-1. At the same stage, X-ngnr-1 expression can be observed in the presumptive trigeminal placode, where X-Delta-1 mRNA is not yet detectable. At neither of these stages is expression of XNeuroD detected (not shown). These data indicate that expression of X-ngnr-1 preceeds that of X-Delta-1 in both the CNS (neural plate) and the PNS (trigeminal placode), whereas XNeuroD is not expressed until after X-Delta-1.

In Drosophila, the proneural genes (achaete-scute) activate expression of Delta (Hinz et al., 1994; Kunisch et al., 1994). The fact that expression of X-ngnr-1 preceeds but spatially overlaps that of X-Delta-1 suggested, therefore, that the former might be capable of activating expression of the latter. In support of this idea, injection of synthetic X-NGNR-1 RNA induced ectopic expression of endogenousX-Delta-1 mRNA (100% of embryos examined; ≧50 embryos injected), whereas control injections of lacZ mRNA had no such effect. Thus, like the proneural genes in Drosophila, X-ngnr-1 can activate expression of a lateral inhibitory ligand that controls a choice between neuronal and non-neuronal fates, within a group of developmentally equivalent cells.

Xnotch1$^{ICD}$ inhibits both the expression and function of X-NGNR-1 Within the three domains of the neural plate, X-ngnr-1 mRNA-expressing cells appear scattered, rather than contiguous. In Drosophila, the expression of achaete-scute is restricted to sensory organ precursor cells by lateral inhibitory interactions mediated by Notch and Delta (Ghysen et al., 1993). This suggested by analogy that the expression of X-ngnr-1 might similarly be restricted to subsets of neural precursors by lateral inhibition. Three different experiments support this idea. First, injection of a dominant-active form of Notch (Struhl et al., 1993) (the intracellular domain, or ICD), which inhibits primary neurogenesis, also repressed the expression of endogenous X-ngnr-1 mRNA (18/18 embryos tested); in contrast control injections of lacZ mRNA had no such effect. Conversely, blocking lateral inhibition by injection of a dominant-negative form of X-Delta-1 (X-Delta-1$^{Stu}$) (Chitnis et al., 1995), caused an apparent increase in the density of strongly X-ngnr-1-positive cells, as well as a slight expansion of the X-ngnr-1-positive domain in 60% of injected embryos (31/50 embryos tested). In contrast such an effect was not seen in control lacZ-injected embryos (except in one isolated case out of 39 embryos examined). This second result suggested that the density of X-ngnr-1-expressing cells within each domain of primary neurogenesis is normally limited by lateral inhibition. The fact that exogenous Notch$^{ICD}$ is, moreover, able to strongly suppress endogenous X-ngnr-1 expression supports the idea that this lateral inhibition is mediated, at least in part, by endogenous X-Notch genes.

To determine whether Notch-mediated signalling can inhibit the function as well as the expression of X-ngnr-1, exogenous X-ngnr-1 mRNA was co-injected with either lacZ mRNA, or lacZ mRNA plus Notch$^{ICD}$ mRNA. An inhibition of X-ngnr-1-promoted ectopic neurogenesis was observed with high penetrance (27/29 embryos tested), indicating that the function as well as the expression of X-NGNR-1 is sensitive to inhibition by Notch$^{ICD}$. However, within the injected side of the experimental embryos, the inhibition of neurogenesis showed variable expressivity, and appeared most complete in those regions which received the highest amount of the co-injected mRNAs (as determined by XGal staining). Assuming that all three co-injected mRNAs are similarly distributed, this result could indicate that a certain threshhold amount of Notch$^{ICD}$ mRNA is necessary to overcome neurogenesis promoted by exogenous X-ngnr-1 mRNA, and/or that there is a non-linear relationship between the amount of Notch$^{ICD}$ mRNA injected and the amount of inhibitory activity produced.

The initial expression of X-ngnr-1 occurs in three territories (medial, intermediate and lateral) which demarcate the domains in which primary neurogenesis will eventually occur (Chitnis et al., 1995). Our data suggest that within these territories, lateral inhibition restricts X-NGNR-1 expression to a limited number of neuronal precursor cells. During this process, X-NGNR-1 positively regulates X-Delta-1, and is in turn negatively regulated (in adjacent cells) by signalling through X-Notch-1, a receptor for X-Delta-1. Thus cells expressing higher levels of X-NGNR-1 will inhibit expression of X-NGNR-1 in their neighbors and thereby suffer less inhibition, leading to yet higher levels of X-NGNR-1 expression, and so on. As X-NGNR-1 expression becomes restricted to presumptive neuronal precursors, it leads (directly or indirectly) to expression of XNeuroD. Once the cells express sufficiently high levels of XNeuroD, they undergo neuronal differentation. In this view, lateral inhibition is part-and-parcel of the cell fate decision process itself, although it may also be engaged to prevent further differentiation after the decision has been made.

This model postulates a role for X-NGNR-1 that is analogous to that deduced for the Drosophila proneural genes, such as achaete-scute and atonal, from both loss-of-function and gain-of-function genetic experiments (Ghysen et al., 1993). While Xenopus is advantageous for gain-of-function perturbations, loss-of-function perturbations are less readily achieved in this system. However our conclusions are not based solely on gain-of-function phenotypes, but also on the timing and place of X-ngnr-1 expression in relation to that of other regulatory genes, as well as on the regulation of endogenous X-ngnr-1 mRNA expression by manipulation of the lateral inhibition machinery.

For example, our conclusion that X-Delta-1 is positively regulated by X-NGNR-1 is consistent with the fact that the initial expression of X-ngnr-1 preceeds and spatially overlaps that of X-Delta-1, as well as with the fact that injection of X-ngnr-1 mRNA induces ectopic expression of endogenous X-Delta-1 mRNA. Similarly, in Drosophila, the proneural genes positively regulate expression of Delta (Hinz et al., 1994; Kunisch et al., 1994). Likewise, our conclusion that expression of X-ngnr-1 is restricted to subsets of cells by lateral inhibition is consistent with the observation that this gene exhibits a scattered pattern of expression within each of the three territories of primary neurogenesis, and that the density of X-NGNR-1 -expressing cells can be increased within these territories by injection of a dominant-negative form of X-Delta-1. Finally, there is a good correlation between the ability of injected X-Delta-1$^{Stu}$ mRNA to increase the density of X-NGNR-1 expressing cells, and also to increase the density of N-tubulin-expressing cells which subsequently differentiate. This correlation suggests that the number of neuronal precursors may normally be determined by the number of cells that express X-NGNR-1 above a given threshhold level.

The observation that X-ngnr-1 both activates, and is inhibited by, the lateral inhibitory circuitry raises the paradox of how a neurogenic phenotype can nevertheless be obtained by over-expressing this gene. The simplest answer is hat the injected X-NGNR-1 RNA bypasses X-Notch-mediated transcriptional repression of the endogenous X-ngnr-1 gene. However, our data suggest that Notch is also able inhibit the function of X-NGNR-1 translated from exogenous RNA, either by a post-transcriptional mechanism or by inhibiting expression of X-NGNR-1 target genes. Nevertheless, this inhibition appears to require high levels of X-Notch$^{ICD}$ expression, being strongest in those regions which contain the highest level of co-injected RNAs. In the situation where X-NGNR-1 RNA alone is injected, the level of endogenous X-Notch signalling may simply be insufficient to override the large amounts of exogenous X-NGNR-1 protein. Moreover, the possibility that Notch$^{ICD}$ inhibits X-NGNR-1 function artefactually, because it is injected in a form that normally does not exist in vivo (see (Nye et al., 1994) for further discussion), cannot be excluded.

Relationship of XASH-3 and X-NGNR-1 Xash3 is the only other neural bHLH gene which is known to be expressed as early as X-ngr-1 in the neural plate (Zimmerman et al., 1993). The available evidence, however, more clearly identifies X-ngnr-1 as a vertebrate analog of the Drosophila proneural genes during primary neurogenesis. Firstly, while the expression of X-ngnr-1 correlates extremely well with the three domains of the neural plate where primary neurons form, Xash-3 is expressed in an "intermediate" zone of the neural plate which may in fact correspond to the sulcus limitans (Zimmerman et al., 1993). Secondly, the activity of Xash3 in ectopic expression studies appears to be different from that of X-NGNR-1. For instance, ectopic expression of XASH-3 at high levels causes an expansion of neural tissue (Ferreiro et al., 1994; Turner and Weintraub, 1994), a phenotype never observed with X-NGNR-1. Ectopic expression of XASH-3 can also induce ectopic neuronal differentiation, but only effectively when lateral inhibition is also blocked using the dominant-negative X-Delta-1, and only then within the posterior neural plate (Chitnis and Kintner, 1996). X-NGNR-1 does not have similar restrictions in its activity, and can promote neurogenesis anteriorly, and outside the neural plate. Finally, although exogenous XASH-3 is sensitive to lateral inhibition mediated by X-Notch-1 and X-Delta-1 (Chitnis and Kintner, 1996), there is no evidence that endogenous Xash-3 expression is normally regulated by such inhibition. Thus, X-ngnr-1 fulifills more of the criteria expected for a gene whose activity defines the "proneural" domains wherein primary neurons arise in the neural plate.

The function of Xash-3 remains enigmatic. The fact that ectopic expression of this gene expands undifferentiated neural tissue suggests that it could normally act to prevent or delay overt neuronal differentiation within the restricted domain of the neural plate where it is expressed. Consistent with this idea, injection of Notch$^{ICD}$ which expands the neural plate also expands the domain of Xash-3 mRNA expression (unpublished observations). This is exactly the opposite of what is observed in the case of X-ngnr-1, whose expression is repressed under these conditions. An insensitivity of Xash-3 to transcriptional inhibition by X-Notch-1 signalling would allow the continued expression of this gene to maintain the uncommitted neural character of neural plate cells, while the high sensitivity of XASH-3 to functional inhibition by Notch (Chitnis and Kintner, 1996) would prevent these cells from undergoing overt neuronal differentiation. Whether XASH-3 also contributes to primary or secondary neurogenesis, but in different cells or at a different step in the pathway as X-NGNR-1, remains to be determined.

X-NGNR-1 performs two distinct and temporally separated functions In our experiments, injection of X-ngnr-1 mRNA results in the induction of both X-Delta-1 and XNeuroD. During normal development, however, expression of XNeuroD is delayed relative to that of X-Delta-1. How is the sequential expression of these two putative target genes of X-NGNR-1 normally achieved? One possibility is that X-Delta-1 requires a lower threshhold of X-NGNR-1 activity than XNeuroD to be activated, and that it takes time for X-NGNR-1 to accumulate to levels sufficient to induce XNeuroD. Another explanation is that a co-factor is required together with X-NGNR-1 to activate XNeuroD, and that expression of this co-factor is delayed. Precedent for such a temporal separation of transcription factor functions is found during mother-daughter segregation in yeast, where the Swi5 protein acts first to activate ASH1 expression (which in turn blocks Swi5p function in daughter cells (Bobola et al., 1996; Sil and Herskowitz, 1996)), and later to activate HO expression in mother cells. The delay in HO activation by Swi5p reflects an induction of the necessary co-activators Swi4p and Swi6p (Amon, 1996). Interestingly, in both Xenopus neurogenesis and yeast the temporal separation provides a time window for these determinative factors (Swi5p or X-NGNR-1) to provide an inhibitory signal to neighboring or daughter cells, while allowing them to later promote an alternative fate cell-autonomously.

Determination versus differentiation genes We have documented a sequential expression of ngn and NeuroD mRNAs during both murine and Xenopus neurogenesis, and in the latter system have further demonstrated a unidirectional functional cascade for these genes. Thus in Xenopus neurogenesis, as in mammalian skeletal myogenesis and Drosophila neurogenesis, structurally-related bHLH proteins function in cascades (Jan and Jan, 1993). The timing and location of NeuroD expression have previously been suggested to reflect a function for this gene in neuronal differentiation (Lee et al., 1995), perhaps analogous to that of myogenin during muscle development (for review, see (Weintraub, 1993)). By extension, the upstream gene X-ngnr-1 would function in determination, analogous to the roles of MyoD and myf5 during myogenesis. Such a conclusion would be consistent with our demonstration that the regulation and function of X-ngnr-1 are similar to that of the proneural genes, which control the determination of neural precursors in *Drosophila* (Campuzano and Modolell, 1992).

What is different about determination and differentiation bHLH factors? The similar actions of these proteins in gain-of-function experiments suggest that they may differ only in the time and place of their expression, or in the downstream genes they regulate (Jan and Jan, 1993). On the other hand, they may possess intrinsic functional differences that have so far escaped detection. For example, it has been proposed that muscle differentiation factors are less sensitive to inhibitors than are determination factors (Weintraub, 1993). However, such a differential sensitivity to inhibitors has not been demonstrated in myogenesis, although MyoD function can be inhibited by Notch$^{ICD}$ (Kopan et al., 1994).

Previously, a differential sensitivity of XASH-3 and XNeuroD to lateral inhibition was demonstrated (Chitnis and Kintner, 1996). Although Xash-3 is expressed earlier than ANeuroD, there is no evidence that the two genes function in a cascade; indeed the latter gene is expressed in many regions where it is not preceeded by the former. While X-NGNR-1 and XNeuroD do appear to function in a cascade, they do not appear differentially sensitive to inhibition by co-injected X-Notch$^{ICD}$, in side-by-side comparisons (Ma et al., unpublished data). It is possible that these genes are differentially sensitive to direct inhibition by Notch signalling at the transcriptional level, but this is currently difficult to test since inhibition of X-NGNR-1 expression by Notch$^{ICD}$ indirectly prevents expression of XNeuroD.

The determination function proposed for X-ngnr-1 may, therefore, primarily reflect the developmental context in which this gene is expressed. Expression of X-ngnr-1 in the neurectoderm generates a group of competent cells, from which a subset is later selected for overt neuronal differentiation. The state of competence imposed by X-ngnr-1 expression is insufficient to allow differentiation, precisely because the expression and function of this gene are sensitive to lateral inhibition. However, through its ability to upregulate X-Delta-1, X-NGNR-1 confers the capacity to engage in a winner-take-all competition between alternative cell states: neuronal or non-neuronal. While increased expression of X-NGNR-1 imposes a bias towards the neuronal state, this state is unstable until subsequent events render the cell insensitive to further inhibition. The nature of the events that stabilize the neuronal state and commit the cell irrerversibly to neuronal differentiation remain to be established.

BIBLIOGRAPHY

Akazawa, et al., (1995) J. Biol. Chem. 270, 8730–8738.
Akazawa, et al., (1992) J. Biol. Chem. 21879–21885.
Amon, A. (1996). Cell. 84, 651–654.
Artavanis-Tsakonas, et al., (1995) Science. 268, 225–232.
Bartholomä, et al., (1994) Mech. Devel. 48, 217–228.
Bobola, et al, (1996) Cell. 84, 699–710.
Brand, et al. (1993) Development. 119, 1–17.
Campuzano, et al., (1 992) Trends Genet. 8, 202–208.
Chitnis, et al., (1995) Nature. 375, 761–766.
Chitnis, et al. (1996) Development. in press,
Chitnis, A. B. (1995) Mol. Cell. Neurosci. 6, 311–321.
Coffman, et al., (1990) Science. 249, 1438–1441.
Coffman, et al., (1993) Cell. 73, 659–671.
Cubas, et al., (1991). Genes & Dev. 5, 996–1008.
Dominguez, et al.,(1993). EMBO J. 12, 2049–2060.
Ferreiro,et al.,(1994). Development. 120,3649–3655.
Ferreiro, et al., (1992). Mech. Development. 40, 25–36.
Ghysen, et al., (1993). Genes & Dev. 7, 723–733.
Guillemot,et al.,(1993). Mech.Devel. 42,171–185.
Guillemot, et al., (1993). Cell. 75, 463–476.
Hinz, et al., (1994). Cell. 76, 77–88.
Ishibashi, et al., (1993). Eur. J. Biochem. 215, 645–652.
Jan and Jan, (1993). Cell. 75,827–830.
Jan, Y. N. and Jan, L. Y. (1994). Ann. Rev. of Genet. 28, 373–393.
Jarman, et al.,(1993a). Development. 119, 19–29.
Jarman, et al.,(1993b). Cell. 73, 1307–1321.
Johnson,et al.,(1990). Nature. 346,858–861.
Kintner, et al.,(1987). Development. 99, 311–325.
Kopan, et al., (1994). Development. 120, 2385–2396.
Kozak, M. (1984). 12, 857–872.
Kume, et al., (1996). Biochem. Biophys. Res. Commun. 219, 526–530.
Kunisch, et al., (1994). Proc. Natl. Acad. Sci. U.S.A. 91, 10139–10143.
Lamb, et al., (1993). Science. 262, 713–718.
Lee, et al., (1995). Science. 268, 836–844.
Lo, et a., (1991). Genes & Dev. 5, 1524–1537.
Naya, et al., (1995). Genes & Dev. 9, 1009–1019.
Nye, et al., (1994). Development. 120, 2421–2430.
Olson, et al., (1994). Genes & Dev. 8, 1–8.
Saito, et al., (1995). Mol. Cell. Neurosci. 6, 280–292.
Sasai, et al., (1992). Genes & Dev. 6, 2620–2634.
Sasai, et al., (1995). Nature. 376, 333–336.
Shimizu, et al., (1995). Eur. J. Biochem. 229, 239–248.
Sil, et al., (1996). Cell. 84, 711–722.
Smith, et al., (1992). Cell. 70,829–840.
Sommer, et al., (1995). Neuron. 15, 1245–1258.
Struhl, et al., (1993). Cell. 74, 331–345.
Turner, et al., (1994). Genes Dev. 8, 1434–1447.
Villares, et al., (1987). Cell. 50, 415–424.
Weintraub, H. (1993). Cell. 75, 1241–1244.
Zimmerman, et al., (1993). Development. 119, 221–232.

We claim:

1. An isolated nucleic acid comprising the nucleic acid sequence of SEQ ID NO:13.

2. An isolated nucleic acid molecule that is at least 80% homoloaous to SEQ ID NO:13.

3. An isolated nucleic acid of claim 2 that is at least 90% homologous to SEQ ID NO:13.

4. An isolated nucleic acid of claim 2 that is at least 95% homologous to SEQ ID NO:13.

5. An isolated nucleic acid of claim 2 that is at least 98% homologous to SEQ ID NO:13.

6. An expression vector comprising transcriptional and translational regulatory DNA operably linked to a nucleic acid of claim 2.

7. A host cell comprising the expression vector or claim 6.

8. A method of producing a neurogenin protein comprising:
  a) culturing a host cell transformed with an expression vector of claim 6;
  b) expressing said nucleic acid to produce a neurogerin protein.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 244 amino acids
      (B) TYPE: amino acid (C) STRANDEDNESS: unknown
        (D) TOPOLOGY: unknown (ii) MOLECULE TYPE: protein (xi) SEQUENCE DESCRIPTION: SEQ ID NO:1:

Met Pro Ala Pro Leu Glu Thr Cys Leu Ser Asp Leu Asp Cys Ala Ser
1               5                   10                  15

Ser Asn Ser Gly Ser Asp Leu Ser Ser Phe Leu Thr Asp Glu Glu Asp
            20                  25                  30

Cys Ala Arg Leu Gln Pro Leu Ala Ser Thr Ser Gly Leu Ser Val Pro
        35                  40                  45

Ala Arg Arg Ser Ala Pro Thr Leu Ser Gly Ala Ser Asn Val Pro Gly
50                  55                  60

Gly Gln Asp Glu Glu Gln Arg Arg Arg Arg Gly Arg Ala Arg
65                  70                  75                  80

Val Arg Ser Glu Ala Leu Leu His Ser Leu Arg Arg Ser Arg Arg Val
                85                  90                  95

Lys Ala Asn Asp Arg Glu Arg Asn Arg Met His Asn Leu Asn Ala Ala
                100                 105                 110

Leu Asp Ala Leu Arg Ser Val Leu Pro Ser Phe Pro Asp Asp Thr Lys
            115                 120                 125

Leu Thr Lys Ile Glu Thr Leu Arg Phe Ala Tyr Asn Tyr Ile Trp Ala
130                 135                 140

Leu Ala Glu Thr Leu Arg Leu Ala Asp Gln Gly Leu Pro Gly Gly Gly
145                 150                 155                 160

Ala Arg Glu Arg Leu Leu Pro Pro Gln Cys Val Pro Cys Leu Pro Gly
                165                 170                 175

Pro Pro Ser Pro Ala Ser Asp Thr Glu Ser Trp Gly Ser Gly Ala Ala
            180                 185                 190

Ala Ser Pro Cys Ala Thr Val Ala Ser Pro Leu Ser Asp Pro Ser Ser
            195                 200                 205

Pro Ser Ala Ser Glu Asp Phe Thr Tyr Gly Pro Gly Gly Pro Leu Phe
        210                 215                 220

Ser Phe Pro Gly Leu Pro Lys Asp Leu Leu His Thr Thr Pro Cys Phe
225                 230                 235                 240

Ile Pro Tyr His (2) INFORMATION FOR SEQ ID NO:2:

(i) SEQUENCE CHARACTERISTICS:
        (A) LENGTH: 214 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:2:

Met Val Leu Leu Lys Cys Glu Tyr Arg Asp Glu Glu Asp Leu Thr
1               5                   10                  15

Ser Ala Ser Pro Cys Ser Val Thr Ser Ser Phe Arg Ser Pro Ala Thr
            20                  25                  30

Gln Thr Cys Ser Ser Asp Asp Glu Gln Leu Leu Ser Pro Thr Ser Pro
        35                  40                  45

Gly Gln His Gln Gly Glu Glu Asn Ser Pro Arg Cys Arg Arg Ser Arg
50                  55                  60

Gly Arg Ala Gln Gly Lys Ser Gly Glu Thr Val Leu Lys Ile Lys Lys
65                  70                  75                  80

Thr Arg Arg Val Lys Ala Asn Asn Arg Glu Arg Asn Arg Met His Asn
                85                  90                  95

Leu Asn Ser Ala Leu Asp Ser Leu Arg Glu Val Leu Pro Ser Leu Pro
                100                 105                 110

Glu Asp Ala Lys Leu Thr Lys Ile Glu Thr Leu Arg Phe Ala Tyr Asn
                115                 120                 125

Tyr Ile Trp Ala Leu Ser Glu Thr Leu Arg Leu Gly Asp Pro Val His
        130                 135                 140

Arg Ser Ala Ser Thr Pro Ala Ala Ile Leu Val Gln Asp Ser Ser
145                 150                 155                 160

Ser Ser Gln Ser Pro Ser Trp Ser Cys Ser Ser Pro Ser Ser Ser
                165                 170                 175

Cys Cys Ser Phe Ser Pro Ala Ser Pro Ala Ser Ser Thr Ser Asp Ser
                180                 185                 190

Ile Glu Ser Trp Gln Pro Ser Glu Leu His Leu Asn Pro Phe Met Ser
                195                 200                 205

Ala Ser Ser Ala Phe Ile
210

(2) INFORMATION FOR SEQ ID NO:3:

(i) SEQUENCE CHARACTERISTICS:
        (A) LENGTH: 57 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

Arg Ser Arg Arg Val Lys Ala Asn Asp Arg Glu Arg Asn Arg Met His
1               5                   10                  15

Asn Leu Asn Ala Ala Leu Asp Ala Leu Arg Ser Val Leu Pro Ser Phe
                20                  25                  30

Pro Asp Asp Thr Lys Leu Thr Lys Ile Glu Thr Leu Arg Phe Ala Tyr
                35                  40                  45

Asn Tyr Ile Trp Ala Leu Ala Glu Thr
50                  55

(2) INFORMATION FOR SEQ ID NO:4:

(i) SEQUENCE CHARACTERISTICS:
        (A) LENGTH: 57 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:4:

Lys Thr Arg Arg Val Lys Ala Asn Asn Arg Glu Arg Asn Arg Met His
1               5                   10                  15

Asn Leu Asn Ser Ala Leu Asp Ser Leu Arg Glu Val Leu Pro Ser Leu
                20                  25                  30

Pro Glu Asp Ala Lys Leu Thr Lys Ile Glu Thr Leu Arg Phe Ala Tyr
                35                  40                  45

Asn Tyr Ile Trp Ala Leu Ser Glu Thr
50                  55

(2) INFORMATION FOR SEQ ID NO:5:

(i) SEQUENCE CHARACTERISTICS:
       (A) LENGTH: 57 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:5:

```
Lys Leu Arg Arg Met Lys Ala Asn Ala Arg Glu Arg Asn Arg Met His
  1               5                  10                  15

Gly Leu Asn Ala Ala Leu Asp Asn Leu Arg Lys Val Val Pro Cys Tyr
             20                  25                  30

Ser Lys Thr Gln Lys Leu Ser Lys Ile Glu Thr Leu Arg Leu Ala Lys
         35                  40                  45

Asn Tyr Ile Trp Ala Leu Ser Glu Ile
 50                  55
```

(2) INFORMATION FOR SEQ ID NO:6:

(i) SEQUENCE CHARACTERISTICS:
       (A) LENGTH: 57 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:6:

```
Lys Phe Arg Arg Gln Glu Ala Asn Ala Arg Glu Arg Asn Arg Met His
  1               5                  10                  15

Gly Leu Asn Asp Ala Leu Asp Asn Leu Arg Lys Val Val Pro Cys Tyr
             20                  25                  30

Ser Lys Thr Gln Lys Leu Ser Lys Ile Glu Thr Leu Arg Leu Ala Lys
         35                  40                  45

Asn Tyr Ile Trp Ala Leu Ser Glu Ile
 50                  55
```

(2) INFORMATION FOR SEQ ID NO:7:

(i) SEQUENCE CHARACTERISTICS:
       (A) LENGTH: 57 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:7:

```
Lys Leu Arg Arg Gln Lys Ala Asn Ala Arg Glu Arg Asn Arg Met His
  1               5                  10                  15

Asp Leu Asn Ala Ala Leu Asp Asn Leu Arg Lys Val Val Pro Cys Tyr
             20                  25                  30

Ser Lys Thr Gln Lys Leu Ser Lys Ile Glu Thr Leu Arg Leu Ala Lys
         35                  40                  45

Asn Tyr Ile Trp Ala Leu Ser Glu Ile
 50                  55
```

(2) INFORMATION FOR SEQ ID NO:8:

(i) SEQUENCE CHARACTERISTICS:
    (A) LENGTH: 57 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:8:

```
Lys Asn Arg Arg Leu Ala Ala Asn Ala Arg Glu Arg Arg Met His
 1               5                  10                  15
Gly Leu Asn His Ala Phe Asp Gln Leu Arg Asn Val Ile Pro Ser Phe
                20                  25                  30
Asn Asn Asp Lys Lys Leu Ser Lys Tyr Glu Thr Leu Gln Met Ala Gln
                35                  40                  45
Ile Tyr Ile Asn Ala Leu Ser Glu Ile
                50                  55
```

(2) INFORMATION FOR SEQ ID NO:9:

(i) SEQUENCE CHARACTERISTICS:
        (A) LENGTH: 57 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:9:

```
Arg Lys Arg Arg Leu Ala Ala Asn Ala Arg Glu Arg Arg Met Gln
 1               5                  10                  15
Asn Leu Asn Gln Ala Phe Asp Arg Leu Arg Gln Tyr Leu Pro Cys Leu
                20                  25                  30
Gly Asn Asp Arg Gln Leu Ser Lys His Glu Thr Leu Gln Met Ala Gln
                35                  40                  45
Thr Tyr Ile Ser Ala Leu Gly Asp Leu
                50                  55
```

(2) INFORMATION FOR SEQ ID NO:10:

(i) SEQUENCE CHARACTERISTICS:
        (A) LENGTH: 54 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:10:

```
Val Ala Arg Arg Asn Glu Arg Glu Arg Asn Arg Val Lys Leu Val Asn
 1               5                  10                  15
Leu Gly Phe Ala Thr Leu Arg Glu His Val Pro Asn Gly Ala Ala Asn
                20                  25                  30
Lys Lys Met Ser Lys Val Glu Thr Leu Arg Ser Ala Val Glu Tyr Ile
                35                  40                  45
Arg Ala Leu Gln Gln Leu
                50
```

(2) INFORMATION FOR SEQ ID NO:11:

(i) SEQUENCE CHARACTERISTICS:
        (A) LENGTH: 68 amino acids
        (B) TYPE: amino acid
        (C) STRANDEDNESS: unknown (D) TOPOLOGY: unknown (ii) MOLECULE TYPE: protein (xi) SEQUENCE DESCRIPTION: SEQ ID NO:11:

Val Ile Arg Arg Asn Ala Arg Glu Arg Asn Arg Val Lys Gln Val Asn
1               5                   10                  15

Asn Gly Phe Ser Gln Leu Arg Gln His Ile Pro Ala Ala Val Ile Ala
            20                  25                  30

Asp Leu Ser Asn Gly Arg Arg Gly Ile Gly Pro Gly Ala Asn Lys Lys
        35                  40                  45

Leu Ser Lys Val Ser Thr Leu Lys Met Ala Val Glu Tyr Ile Arg Arg
    50                  55                  60

Leu Gln Lys Val
65

(2) INFORMATION FOR SEQ ID NO:12:

(i) SEQUENCE CHARACTERISTICS:
        (A) LENGTH: 1527 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:12:

| | | | | | |
|---|---|---|---|---|---|
| ATCCGGAGCT | GATCTGATCG | CCGGCGACAT | CAGTCGGGAG | ACCAGCCCGG | CGCGTGGCCC | 60 |
| CCTGCAGGCG | AGGCGAGGAG | GCCAAGCCCA | TTCCCTCCCT | GAGCCCCTGC | GATCTTCCCC | 120 |
| GGCCCTCGCG | CCTGCAGCAG | GCACAGGCTA | GCCCCGGGTC | ATACGGACAG | TAAGTGCGCT | 180 |
| TCGAAGGCCG | TGCACTCGGC | CCACATTCAA | GCCCTCCAAA | CCTCCCGTCC | GTCCGTCCGT | 240 |
| CCTGCAACGA | TGCCTGCCCC | TTTGGAGACC | TGTCTCTCTG | ACCTCGACTG | CGCCAGCAGC | 300 |
| AACAGCGGGA | GCGACCTGTC | CAGTTTCCTC | ACCGACGAGG | AGGACTGTGC | CAGGCTCCAG | 360 |
| CCCCTAGCTT | CCACCTCAGG | GCTGTCCGTG | CCAGCCCGCA | GGAGCGCGCC | CACCCTCTCC | 420 |
| GGGGCATCGA | ACGTTCCCGG | TGGCCAGGAC | GAAGAGCAGG | AGCGGCGGCG | ACGGCGAGGT | 480 |
| CGCGCGCGGG | TGCGGTCCGA | GGCGCTGCTG | CACTCGCTGC | GGAGGAGCCG | TCGCGTCAAG | 540 |
| GCCAACGATC | GCGAGCGCAA | CCGTATGCAT | AACCTCAACG | CTGCGCTGGA | CGCTCTGCGC | 600 |
| AGCGTGCTGC | CCTCGTTCCC | CGACGACACC | AAGCTCACCA | AGATTGAGAC | GCTGCGCTTC | 660 |
| GCCTACAACT | ACATCTGGGC | CCTGGCTGAG | ACACTGCGCC | TGGCAGATCA | AGGGCTCCCG | 720 |
| GGGGGCGGTG | CCCGGGAGCG | CCTCCTGCCT | CCGCAGTGTG | TCCCCTGCCT | GCCCGGTCCC | 780 |
| CCGAGCCCGG | CCAGCGATAC | AGAGTCCTGG | GGCTCCGGGG | CCGCTGCCTC | CCCCTGCGCT | 840 |
| ACTGTGGCGT | CACCACTCTC | TGACCCCAGT | AGTCCCTCGG | CTTCAGAAGA | CTTCACCTAT | 900 |
| GGCCCGGGTG | GTCCCCTTTT | CTCCTTTCCT | GGCCTGCCCA | AGACCTCCT | CCATACGACA | 960 |
| CCCTGCTTCA | TCCCGTACCA | CTAGGGCTTT | GCAAGACAAC | GTTAATACTT | CTTTCCTGCC | 1020 |
| CCAGTCTATG | AGCAATAGAT | GGGGGAGCCG | GCTGAAGCCT | CGGGGAGCAC | CCTTACCCCC | 1080 |
| AGGTGGATGC | TGGGAGCTTT | AAAGAGGGGA | GGGATACCTG | ACCACTTGCT | AGGTTGCCGC | 1140 |
| ACCCTCGCTG | AGAAGCTGCC | CCTCGGACTG | TTTCCCCACG | CCCCAGCACC | GGGCCCCTCC | 1200 |
| TGCCCGCCCC | CCAGACGGGC | TTTCGGTTTT | TTTTTTGGAC | TTCCTGAACT | TCACAAAACC | 1260 |
| TCCTTTGTGA | CTGGCTCAGA | ACTGACCCCA | GCCACCACTT | CAGTGTGATT | TGGAAAAGGG | 1320 |
| ACAGATGAGC | CCCTGAAGAC | GAGGTGAAAA | GTCAATTTTA | CAATTTGTAG | AACTCTAATG | 1380 |

```
AAGAAAAACG AGCATGAAAA TTCGGTTTGA GCCGGCTGAC AATACAATGA AAAGGCTTAA       1440

AAAAAAGGAG ACACAAGGAG TGGGCTTCAT GCATTATGGA TCCCGACCCC CACCACTGTG       1500

GGCTTGCTCC CGGAAGAACT GAGTGCT                                          1527
```

(2) INFORMATION FOR SEQ ID NO:13:

(i) SEQUENCE CHARACTERISTICS:
        (A) LENGTH: 738 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:13:

```
ATGCCTCCCC CTTTGGAGAC CTGCATCTCT GATCTCGACT GCTCCAGCAG CAACAGCAGC         60

AGCGACCTGT CCAGCTTCCT CACCGACGAG GAGGACTGTG CCAGGCTACA GCCCCTAGCC        120

TCCACCTCGG GGCTGTCCGT GCCAGCCCGG AGGAGCGCTC CCGCCCTCTC CGGGGCATCG        180

AATGTTCCCG GTGCCCAGGA CGAAGAGCAG GAACGGCGGA GGCGGCGAGG TCGCGCTCGG        240

GTGCGGTCCG AGGCTCTGCT GCACTCCCTG CGGAGGAGTC GTCGCGTCAA AGCCAACGAT        300

CGCGAGCGCA ACCGCATGCA CAACCTCAAC GCTGCGCTGG ACGCCTTGCG CAGCGTGCTG        360

CCCTCGTTCC CCGACGACAC CAAGCTCACC AAGATTGAGA CGCTGCGCTT CGCCTACAAC        420

TACATCTGGG CCCTGGCTGA GACACTGCGC CTGGCAGATC AAGGGCTCCC CGGGGGCAGT        480

GCCCGGGAGC GCCTCCTGCC TCCGCAGTGT GTCCCCTGTC TGCCCGGGCC CCCGAGCCCG        540

GCCAGCGACA CTGAGTCCTG GGGTTCCGGG GCCGCTGCCT CCCCCTGCGC CACTGTGGCA        600

TCACCACTCT CTGACCCCAG TAGTCCCTCG GCTTCAGAAG ACTTCACCTA TGGCCCGGGC        660

GATCCCCTTT TCTCCTTTCC TGGCCTGCCC AAAGACCTGC TCCACACGAC GCCCTGTTTC        720

ATCCCATACC ACTAGTAA                                                    738
```

(2) INFORMATION FOR SEQ ID NO:14:

(i) SEQUENCE CHARACTERISTICS:
        (A) LENGTH: 1312 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:14:

```
GCGTGTCACA CGGCAGTTGC ACTCATAATA CACTGTGAGC TGACAGTCGC AACCACGCCC         60

GACAGGGAAC ACGCAGCAAG TCTACTGCAC GACTATAACC CGACGACTCG ACCCAACTCA        120

CCTGCTGCTT CAGGGGCCAA ACACCAAGTT ATAAAGTAAG TAACTTCCAT TGCAACTGCA        180

GCATTGTCAC TTGCGACAGC GCATGAAGTA GTGAGAGGCA CAGACCATGT ACATATATGG        240

GGTTTGTGGT TATTATAGTA AGTGGGATGA TGTTTGGGTT ATTATAGTAA GTGGATGTGA        300

AGTTGTCAGT GCAACATTGG GGCTAACCAT TGGCTGTGTG TTTGCGCTTG TCTAGGATGG        360

TGCTGCTCAA GTGCGAGTAC CGCGATGAAG AGGAGGACCT GACCTCTGCC TCCCCCTGCT        420

CCGTGACCTC CTCTTTCCGT TCCCCGGCGA CGCAGACGTG CAGCTCGGAC GATGAGCAGC        480

TCCTGAGTCC CACCAGCCCG GGACAGCACC AGGGGGAAGA GAACAGCCCG CGATGCAGGA        540

GGAGCCGAGG CCGCGCTCAG GGCAAGAGCG GAGAAACTGT GTTAAAGATC AAGAAGACCC        600
```

-continued

```
GGCGCGTTAA AGCTAACAAC CGGGAAAGGA ATCGCATGCA CAACCTGAAC TCTGCGCTTG       660

ATTCCCTCAG GGAAGTGTTG CCCTCTTTAC CTGAAGATGC CAAACTCACC AAGATAGAGA       720

CCTTGCGCTT TGCCTACAAC TACATCTGGG CTCTTAGCGA AACTTTGCGC CTTGGCGACC       780

CAGTGCACCG ATCTGCTTCC ACCCCAGCAG CAGCCATATT GGTGCAGGAC TCCTCTTCAT       840

CCCAGAGCCC CTCCTGGAGC TGCAGCTCGT CCCCTTCTTC CTCTTGTTGC TCCTTCTCCC       900

CGGCCAGCCC TGCCAGCTCC ACCTCGGACA GTATTGAGTC CTGGCAGCCC TCTGAGCTCC       960

ACCTGAACCC CTTCATGTCT GCCAGCAGCG CTTTCATTTG AACTCCTGTT GGACTATGAT      1020

GGATTCTCAC ACTTCCAATT GCTACATATG AAGAATACCT CAGTGGGGCC CCAGTGCAAA      1080

TGATTTTCCT GGGAACCCAG TTTATTGAGC ATGAGCCCAT ATAGTGTAAT AATATCATCC      1140

TGCAGTGACC AAATTGCACT CTGTGGGTTC TGCTGATGGG GAGAAGTGGG GGGCTTGATC      1200

CCCCTGAGTT TGTGCTTACC TGTATAGCAT TTACTCCCCC TGCTGTCATG CCCCTGGCAT      1260

ATGATGGAGT ACATTGCTGG GTCTATTTTA TTATCAGCAA TGTGAACTGA AA             1312
```

(2) INFORMATION FOR SEQ ID NO:15:

(i) SEQUENCE CHARACTERISTICS:
        (A) LENGTH: 1277 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:15:

```
CGAGTGCGCA ACACTTGAGC TGGAGTGCGG GGCGCGTGTC ACACACACAC TGAACTGCCA        60

CTGACACCAG AGACACAGCG AGTGGGAACC CCCTGCTACT ACAGGACTAG GAGAAAAGCC       120

GCACAGCCTG CAGCGCCGCA ACCCGACTCA CCTGCTGCTC CCGGAGCCAC AAGCCTGGCG       180

CACAAGATGG TGCTGCTGAA GTGCGAATAC CGCGATGAGG TGTCGGAACT GACCTCTGTC       240

TCCCCCTGCT CCGTGTCCTC CTCCTCTTCA CACCCGTCCC CGGCGATGCA GACGTGCAGC       300

TCGGACGATG AGCAGCTACA CAGTCCGACA AGCCCGACGC TCACGCACCT GCAGCAGGGA       360

CGGGACCAGG GGGAGGAGAA CAGCCCGCGA TGCAGGAGGA GCCGAGCCCG CGGAGACACC       420

GTGCTGAAGA TCAAGAAGAC CCGGCGCGTT AAAGCCAATA ACGCGAGAG GAATCGCATG       480

CACCACCTGA ACTATGCGCT CGATTCTCTG AGGGAGGTTC TACCGTCATT ACCCGAAGAC       540

GCCAAACTCA CCAAGATAGA GACCTTGCGC TTTGCCCACA ACTACATCTG GCTCTTAGC       600

GAAACTTTGC GCCTGGCCGA CCAGCTGCAC GGATCTACTT CCACCCCAGC AGCAGCCATA       660

TTGGTACAGG ACTCCTATCC TTCCCTGAGC CCCTCCTGGA GCTGCAGCTC GTCCCCATCC       720

TCCAACTCTT GCGACTCCTT CTCCCCGACC AGCCCTGCCA GCTCCACCTC GGACAGTATT       780

GAGTACTGGC AGCCCTCTGA GCTCCGCTTG AACCCCTTCA TGTCTGCCCT TTGAACGCAC       840

AGGACTATGG GTGATTTTAA CTTTTTACAC TTTAAATTCC TGCTTCCCAT AAGGGTCAAG       900

TACTGCAGGG GTTACATATC AAGTTTACCT CAGGGGGGGC CACAGCAAAT TCTTTTCCTG       960

GGCCCTAAAA TGTCCTCTGA ATTTGAGCCC ATATAGTGCA ATGGTATAAC CCTGCAATGG      1020

TATAATCCAG CAATGGTATA ATCCTGCATC GTTACCTAAT TGTACTTTGT GGGGTCTGCT      1080

GATGGGGGAC AAGTGTTTGA CCTGTGTCCA GAGTTTCACA TTTACTCCCC CTTTTGGTAT      1140

ATCTCTGGCC GCAACACTTG CTGTGTCTGT TTCATCGTTA GCTATGTGTA TTAGGAAACT      1200

GTCTATCCCT CATCTGCACC TGTTAGACTA CAGCTACCAA CTTCCTGTTA CCAGGGGCT      1260
```

```
ACTGGGTAAT GTACTTC                                                   1277

(2) INFORMATION FOR SEQ ID NO:16:

(i) SEQUENCE CHARACTERISTICS:
          (A) LENGTH: 25 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO:16:

CGCGGATCCM GNAAYGARMG BGARM                                            25

(2) INFORMATION FOR SEQ ID NO:17:

(i) SEQUENCE CHARACTERISTICS:
          (A) LENGTH: 26 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO:17:

CGCGGATCCG CNAAYGCHMG BGARMG                                           26

(2) INFORMATION FOR SEQ ID NO:18:

(i) SEQUENCE CHARACTERISTICS:
          (A) LENGTH: 29 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO:18:

CCGGAATTCG TYTCVAYYTT RCTVADYTT                                        29

(2) INFORMATION FOR SEQ ID NO:19:

(i) SEQUENCE CHARACTERISTICS:
          (A) LENGTH: 29 base pairs
          (B) TYPE: nucleic acid
          (C) STRANDEDNESS: unknown
          (D) TOPOLOGY: unknown (ii) MOLECULE TYPE: DNA (xi) SEQUENCE DESCRIPTION: SEQ ID NO:19:

CCGGAATTCG TYTCVAYYTT DGAVAVYTT                                        29

(2) INFORMATION FOR SEQ ID NO:20:

(i) SEQUENCE CHARACTERISTICS:
          (A) LENGTH: 7 amino acids
          (B) TYPE: amino acid
          (C) STRANDEDNESS: unknown
          (D) TOPOLOGY: unknown (ii) MOLECULE TYPE: protein (ix) FEATURE:
          (A) NAME/KEY: Modified-site
          (B) LOCATION: 2..3
          (D) OTHER INFORMATION: /note= "The 'xaa' at position 2
               represents either Leucine or Methionine."
```

```
    (ix) FEATURE:
          (A) NAME/KEY: Modified-site
          (B) LOCATION: 5..6
          (D) OTHER INFORMATION: /note= "The 'xaa' at position 5
              represents either Valine or Isoleucine."

(xi) SEQUENCE DESCRIPTION: SEQ ID NO:20:

Lys Xaa Ser Lys Xaa Glu Thr
1               5
```